United States Patent [19]
Noda et al.

[11] Patent Number: 5,395,628
[45] Date of Patent: Mar. 7, 1995

[54] CONTROLLED RELEASE SUCCINIC ACID MICROCAPSULES COATED WITH AQUEOUS ACRYLICS

[75] Inventors: Kazuo Noda, Takarazuka; Yoshiyuki Hirakawa, Kobe; Hiroyuki Yoshino, Suita; Shinji Narisawa, Takatsuki, all of Japan

[73] Assignee: Tanabe Seiyaku Co., Ltd., Osaka, Japan

[21] Appl. No.: 870,195

[22] Filed: Apr. 13, 1992

Related U.S. Application Data

[63] Continuation of Ser. No. 627,130, Dec. 13, 1990, abandoned.

[30] Foreign Application Priority Data

Dec. 28, 1989 [JP]  Japan ................... 1-344633

[51] Int. Cl.⁶ ............................................. A61K 9/50
[52] U.S. Cl. ................................. 424/490; 424/468; 424/474; 424/487
[58] Field of Search .............. 424/464, 465, 468, 477, 424/482, 490

[56] References Cited

U.S. PATENT DOCUMENTS

| | | | |
|---|---|---|---|
| 4,427,648 | 1/1984 | Brickl et al. | 424/16 |
| 4,737,357 | 4/1988 | Lehmann et al. | 424/487 |
| 4,820,521 | 4/1989 | Panoz et al. | 424/458 |
| 4,940,588 | 7/1990 | Sparks et al. | 424/490 |

FOREIGN PATENT DOCUMENTS

| | | |
|---|---|---|
| 0122077 | 10/1984 | European Pat. Off. |
| 0156077 | 10/1985 | European Pat. Off. |
| 0156243 | 10/1985 | European Pat. Off. |
| 0181515 | 5/1986 | European Pat. Off. |
| 0225085 | 6/1987 | European Pat. Off. |
| 0262422 | 8/1987 | European Pat. Off. |
| 88/03795 | 6/1988 | WIPO |

OTHER PUBLICATIONS

Documentation from Röhm Pharma, "EUDRAGIT® RL/RS-Dispersionen"; Vorläufiges Merkblatt.

Documentation from Rohm Pharma GmbH Co., "Eudragit RL30D and RS30D: Aqueous Acrylic Resin Dispersion-Application in the Production of Pharmaceutical Preparations", Prospectus (Infor RL/RSD-1/e), pp. 1–7.

R. S. Okor, W. Anderson, "Communications: Casting solvent effects on the permeability of polymer films of differing quaternary ammonium (cation) content", J. Pharm. Pharmacol, (1987) 39, pp. 547–548.

*Primary Examiner*—Thurman K. Page
*Assistant Examiner*—Neil Levy
*Attorney, Agent, or Firm*—Browdy and Neimark

[57] ABSTRACT

A controlled release pharmaceutical preparation comprising (a) a core containing a pharmaceutically active substance and an organic acid, and (b) a coating film formed on the surface of the core by aqueous coating of a water-insoluble and water-slightly permeable acrylic polymer containing a trimethylammonium-ethyl group, which exhibits well controlled dissolution and release of the pharmaceutically active substance when administered and can maintain the desired blood level of the active substance for a long period of time, and a method for producing the preparation.

12 Claims, 1 Drawing Sheet

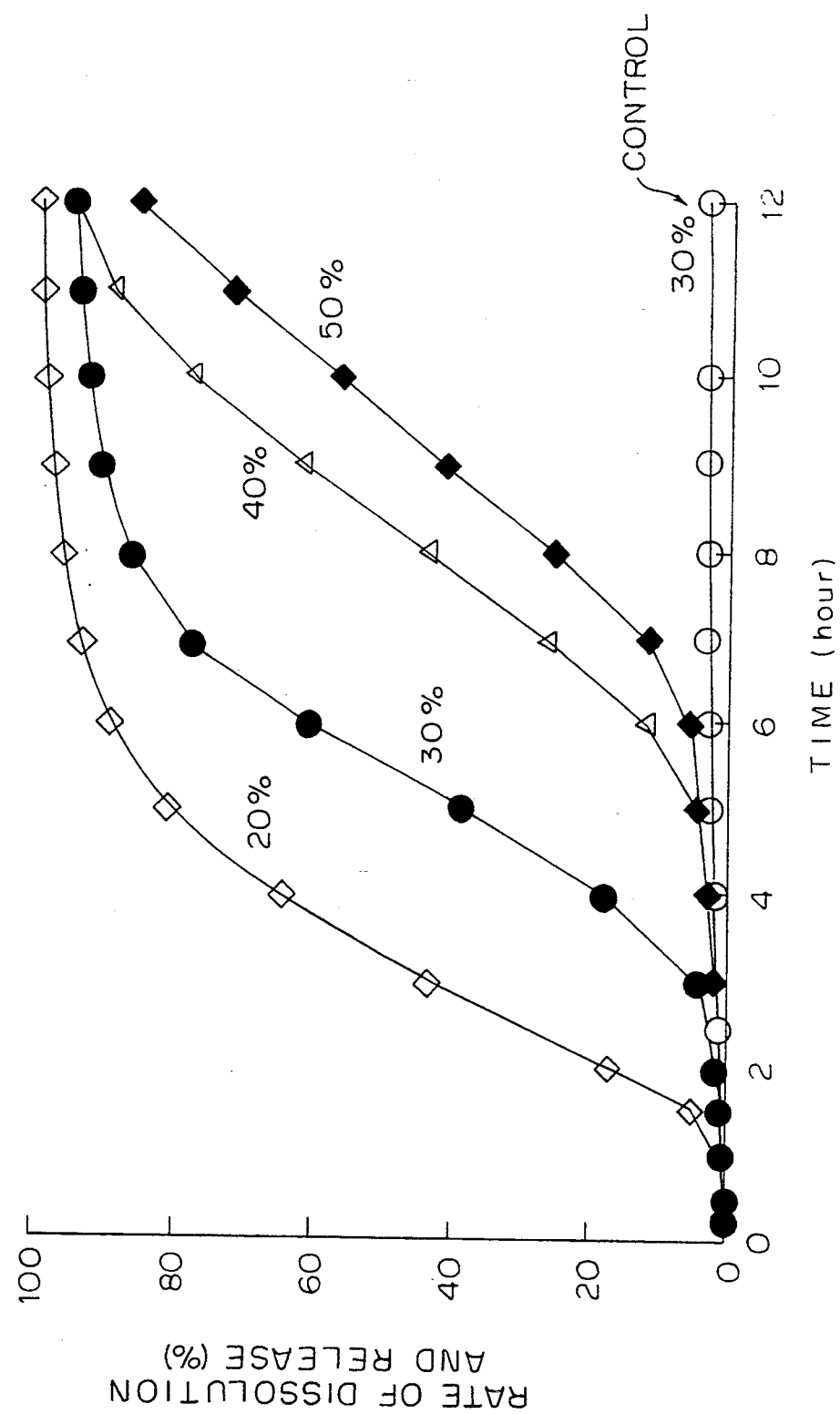

CONTROLLED RELEASE SUCCINIC ACID MICROCAPSULES COATED WITH AQUEOUS ACRYLICS

This application is a continuation of application Ser. No. 07/627,130, filed Dec. 13, 1990, now abandoned.

TECHNICAL FIELD

This invention relates to a controlled release pharmaceutical preparation and a method for producing the same. More particularly, it relates to a controlled release pharmaceutical preparation comprising (a) a core containing a pharmaceutically active substance and an organic acid, and (b) a coating film formed on the surface of the core by aqueous coating of a water-insoluble and water-slightly permeable acrylic polymer containing a trimethylammonium-ethyl group, and a method for producing the same.

PRIOR ART

There is known a sustained-release pharmaceutical preparation which is formed by spray coating a core substance containing a pharmaceutically active substance and an organic acid with an ethanol solution of an acrylic polymer containing a trimethylammonium-ethyl group (cf. Japanese Patent First Publication (Kokai) No. 193913/1985). This method is suitable for dissolving and releasing gradually the pharmaceutically active substance when administered, but it is difficult to control the initiation time of dissolving and releasing thereof.

It is also known that when a coating film applied to a pharmaceutical preparation has a larger thickness, the initiation time of dissolving and releasing of the pharmaceutically active substance can be delayed, but the thick coating film affects release of the active substance and hence the desired blood level of the active substance is not obtained soon after the initiation of the dissolving and releasing thereof.

There is also known a delayed-release pharmaceutical form comprising spheroid particles or tablets containing a pharmaceutically active substance (bromhexine or salt thereof) and a pharmacologically acceptable acid or acidic substance and a coating surrounding said spherioid particles or tablets formed with acid-insoluble lacquers soluble in intestinal juices (e.g. a copolymer of methacrylic acid and methacrylic acid ester) or a mixture of the acid-insoluble lacquers and lacquers insoluble in gastric and intestinal juices (e.g. hydroxypropyl methylcellulose phthalate) (cf. U.S. Pat. No. 4,438,091). However, this method can still not control the initiation time of dissolving and releasing of the active substance.

SUMMARY DESCRIPTION OF THE INVENTION

The present inventors have intensively studied as to a pharmaceutical preparation which can show well controlled release of the pharmaceutically active substance and found that when a core containing a pharmaceutically active substance and an organic acid is coated with an aqueous solution of a water-insoluble and water-slightly permeable acrylic polymer containing trimethylammonium-ethyl group, there can be obtained the desired controlled release preparation which can inhibit the dissolution and release of the pharmaceutically active substance for a fixed period of time and can rapidly release the active substance after the initiation of dissolving and releasing thereof and further can maintain the desired blood level of the active substance for a long period of time.

An object of the invention is to provide an improved controlled release pharmaceutical preparation which can control the dissolution and release of the pharmaceutically active substance and maintain the desire blood level thereof for a long period of time. Another object of the invention is to provide a method for producing the controlled release pharmaceutical preparation. These and other objects and advantages of the invention will be apparent to those skilled in the art from the following description.

BRIEF DESCRIPTION OF THE DRAWINGS

The accompanying FIG. 1 shows the test results of dissolution and release of the pharmaceutically active substance from the theophylline-containing controlled release granules having different amounts of the coating film as prepared in Experiment, which test was done by paddle method. In the figure, the numeral % means the ratio of coating film to the core.

DETAILED DESCRIPTION OF THE INVENTION

The controlled release pharmaceutical preparation of this invention comprises (a) a core containing a pharmaceutically active substance and an organic acid, and (b) a coating film formed on the surface of the core by aqueous coating of a water-insoluble and water-slightly permeable acrylic polymer containing trimethylammonium-ethyl group.

The acrylic polymer composing the coating film includes polymers of acrylic acid, methyl acrylate, ethyl acrylate, methacrylic acid, methyl methacrylate, ethyl methacrylate, etc. which contain trimethylammonium-ethyl group within the molecule thereof. Specific example is a copolymer of ethyl acrylate, methyl methacrylate and trimethylammonium-ethyl methacrylate chloride, wherein the trimethylammonium-ethyl methacrylate chloride is contained in about 0.025–0.033 mole per 1 mole of the remaining neutral acrylic monomers. Such an acrylic polymer is available under the name Eudragit RS ® (manufactured by Röhm Pharma, Germany). The above acrylic polymer may be used alone or by combination with a small amount of a water-permeable polymer, for example, Eudragit RL ® (manufactured by Röhm Pharma, Germany).

The organic acid to be contained in the core together with a pharmaceutically active substance includes citric acid, succinic acid, fumaric acid, malic acid, tartaric acid, glutaric acid, and the like, among which preferred ones are succinic acid, fumaric acid, malic acid and glutaric acid, the most preferred one is succinic acid. The organic acid is contained in an amount of 0.05 to 0.8 parts by weight, preferably 0.1 to 0.6 parts by weight, based on the weight of the core.

The core to be coated may be in any form such as naked tablets, pills, granules, fine granules, and is preferably granulated products having an average particle size of about 300 $\mu$m to about 2,000 $\mu$m, more preferably of about 500 $\mu$m to about 1,500 $\mu$m.

The pharmaceutically active substance to be contained in the core includes any medicament which can be administered in oral route, for example, chemotherapeutic agents, antibiotics, respiratory stimulants, antitussive and antiemetic agents, anti-tumor agents, autonomic agents, psychotroic agents, local anesthetics, muscle relaxants, agents affecting digestive organs, antihistamines, antidotes, hypnotics and sedatives, antiepileptics, antipyretics, analgesics and anti-inflammatory agents, cardiotonics, antiarrhythmic agents, diuretics, vasodilators, antilipaemics, nutrients, tonics and alteratives, anticoagulants, agents for liver diseases, antidiabetics, antihypertensives, and the like. The pharmaceutically active substance is contained in an amount suitable for exhibiting the desired pharmacological activities of each medicament, which has been known and varies in accordance with the kinds of the medicament.

The core may also be incorporated with various conventional additives, such as excipients, binding agents, lubricants, agglomeration inhibitors, and the like.

The excipients include saccharides (e.g. sucrose, lactose, mannitol, glucose, etc.), starches, crystalline cellulose, calcium phosphate, and the like. The binding agents include polyvinyl alcohol, polyvinylpyrrolidone, sucrose, dextrin, hydroxyethyl cellulose, hydroxypropyl cellulose, macrogols (=polyethylene glycols), gum arabic, gelatin, agar, starches, and the like. The lubricants and agglomeration inhibitors include talc, magnesium stearate, calcium stearate, colloidal silica, stearic acid, waxes, hydrogenated oils, polyethylene glycols, sodium benzoate, and the like.

The coating film is formed in such an amount that the acrylic polymer composing the coating film is contained in a range of about 0.3 to 10 parts by weight, preferably about 0.4 to 5 parts by weight, per 1 part by weight of the organic acid contained in the core. When the ratio of the organic acid is increased, the preparation shows more rapid release of the pharmaceutically active substance.

The preparation of this invention can be prepared by coating a core containing a pharmaceutically active substance and an organic acid in the form of naked tablets, granules, pills or fine granules with an aqueous dispersion of a water-insoluble and water-slightly permeable acrylic polymer containing trimethylammonium-ethyl group.

The core can be prepared by a conventional method as disclosed, for example, Remington's Pharmaceutical Science, Vol. 17, 1603-1632, 1633-1643, issued by Mark Publishing Company, 1985. For example, a mixture of a pharmaceutically active substance and an organic acid and optionally further other additives such as excipients, binding agents, lubricants, and the like is subjected to wet extrusion granulation, dry granulation, or the like. Alternatively, a binding agent is dissolved in an appropriate solvent such as water, a lower alcohol (e.g. methyl alcohol, ethyl alcohol, propyl alcohol, isopropyl alcohol, butyl alcohol, etc.), a lower alkanone (e.g. acetone, methyl ethyl ketone, etc.), chloroform, dichloromethane, dichloroethane, and the like, and the solution is coated onto inert carrier particles together with a pharmaceutically active substance and an organic acid by centrifugal fluidization coating, pan coating, fluidized bed coating, or the like, that is, by spraying the solution of binding agent onto the inert carrier particles while adding portionwise a mixture of a pharmaceutically active substance and an organic acid and optionally other additives such as excipients, lubricants and the like.

Besides, the pharmaceutically active substance and the organic acid are not necessarily applied to in the form of a mixture thereof, but they may be applied separately so as to form two or more layers, for example, by firstly adhering the organic acid onto the inert carrier particles (core) to form a layer of the organic acid and thereafter adhering thereon the pharmaceutically active substance, vice versa, i.e. by firstly forming a layer of the pharmaceutically active substance onto the inert carrier particles and thereafter forming thereon a layer of the organic acid.

Alternatively, the organic acid is adhered onto the carrier particles to form a layer of an organic acid and thereon an organic acid-release control film comprising a water-insoluble substance (e.g. ethyl cellulose, waxes such as hydrogenated oils) is formed, and further a layer of a pharmaceutically active substance is formed thereon.

The inert carrier particles include particles of carrier substance, such as sucrose, lactose, starches, crystalline cellulose, and the like.

The coating of the acrylic polymer can be carried out by spraying the aqueous dispersion of the acrylic polymer onto the core containing a pharmaceutically active substance and an organic acid. For instance, the coating can be carried out by a conventional coating method which is usually used in the preparation of pharmaceutical preparations, such as fluidized bed coating, pan coating, or the like. When the coating is carried out by fluidized bed coating, the core is fluidized within an apparatus with air pressure, during which an aqueous dispersion of an acrylic polymer is sprayed through a nozzle of a spray gun onto the core.

The concentration of the acrylic polymer in the aqueous dispersion is not critical but preferable in the range of about 5 to 40 w/w % by weight. The aqueous dispersion of the acrylic polymer may contain other ingredients such as plasticizers, colorants, and the like. The plasticizers include triacetin, triethyl citrate, acetyltributyl citrate, diethyl phthalate, polyethylene glycol, polysorbate, and the like. The plasticizers may be used in an amount of about 5 to 50 w/w % by weight based on the weight of the acrylic polymer.

The aqueous dispersion of acrylic polymer may also contain a few amounts of a hydrophilic organic solvent (e.g. ethanol, methanol, isopropanol, acetone., etc.) and further agglomeration inhibitors (e.g. talc, titanium dioxide, etc.).

After coating, the thus-formed coating film can easily be cured by heat-treatment at a temperature of about 35° to 100° C., preferably 40° to 70° C.

EXAMPLES

The present invention is illustrated by the following examples and experiments but should not be construed to be limited thereto.

Example 1

Nonpareil 103 (trade name of spherical granules of sucrose, manufactured by Freund) (particle size: 710-840 μm, 500 g) is entered and rolled in a centrifugal fluidized granulator (CF-360 EX, manufactured by Freund) and thereto is gradually added a mixture of theophylline fine powder (300 g) and fumaric acid (500 g) while spraying a solution of sucrose (240 g) in water-ethanol (3:1) (720 g), by which the nonpareil is surrounded and coated with the active substance and organic acid to give theophylline-containing granules.

The theophylline granules thus prepared (200 g) are entered into a fluidized bed coating machine (Flow Coater Mini, manufactured by Freund) and thereto is sprayed a coating liquid consisting of Eudragit RS 30 D ® (manufactured by Röhm Pharma, Germany) (168 g), talc (25 g), triethyl citrate (5 g) in water (234 g) with hot air-blowing of 60° C. Thereafter, the mixture is heat-treated at 60° C. to give controlled release theophylline-containing granules (280 g).

Example 2

Nonpareil 103 (particle size: 500-710 μm, 400 g) is entered and rolled in a centrifugal fluidized granulator (CF-360 EX), and thereto is gradually added a mixture of fine powder of (+)--(2S,3S)-3-acetoxy-8-chloro-5-[2-(dimethylamino)ethyl]-2,3-dihydro-2-(4-methoxyphenyl)-1,5-benzothiazepin-4(5H)-one maleate (240 g) (400 g) while spraying a solution of sucrose (190 g) in water-ethanol (3:1) (570 g), by which the nonpareil is surrounded and coated with the active substance and organic acid to give granules.

The granules thus prepared (200 g) are entered into a fluidized bed coating machine (Flow Coater Mini) and thereto is sprayed a coating liquid consisting of Eudragit RS 30 D ® (168 g), talc (25 g), triethyl citrate (5 g) in water (234 g) with hot air-blowing of 60° C. Thereafter, the mixture is heat-treated at 60° C. to give controlled release granules (280 g) containing the above pharmaceutically active substance.

Example 3

By using the same materials as in Example 1 except that fumaric acid is replaced by citric acid (400 g), there are prepared theophylline-containing controlled release granules (280 g) in the same manner as described in Example 2.

Example 4

By using the same materials as in Example 1 except that fumaric acid is replaced by malic acid (400 g), there are prepared theophylline-containing controlled release granules (280 g) in the same manner as described in Example 2.

Example 5

Nonpareil 103 (particle size: 500-710 μm, 500 g) is entered and rolled in a centrifugal fluidized granulator (CF-360 EX), and thereto is gradually added fine particles of succinic acid (500 g) while spraying a solution of sucrose (200 g) in water-ethanol (3:1) (360 g) to give succinic acid-containing granules.

To the granules thus prepared (1000 g) is sprayed a solution of ethyl cellulose (40 g) in water-ethanol (3:7) (360 g), and the resultant is dried at 45° C. to give granules (1040 g) of succinic acid coated with ethyl cellulose.

The ethyl cellulose-coated succinic acid granules thus prepared (500 g) are entered and rolled in a centrifugal fluidized granulator (CF-360 EX), and thereto is gradually added a mixture of fine powder of (+)--(2S,3S)-3-acetoxy-8-chloro-5-[2-(dimethylamino)ethyl]-2,3-dihydro-2(4-methoxyphenyl)-1,5-benzothiazepin-4(5H)-one maleate (300 g) and succinic acid (300 g) while spraying a solution of sucrose (100 g) in water-ethanol (3:1) (300 g) to give granules coated with the pharmaceutically active substance and succinic acid.

The granules thus prepared (200 g) are entered into a fluidized bed coating machine (Flow Coater Mini) and thereto is sprayed a coating liquid consisting of Eudragit RS 30 D ® (168 g), talc (25 g), triethyl citrate (5 g) in water (234 g) with hot air-blowing of 60° C. Thereafter, the mixture is heat-treated at 60° C. to give controlled release granules (280 g) containing the above pharmaceutically active substance.

Example 6

Nonpareil 103 (particle size: 500-710 μm, 500 g) is entered and rolled in a centrifugal fluidized granulator (CF-360 EX), and thereto is gradually added a mixture of fine powder of chlorpheniramine maleate (300 g) and glutaric acid (500 g) while spraying a solution of sucrose (160 g) in water-ethanol (3:1) (480 g), by which the nonpareil is coated therewith to give granules.

The granules thus prepared (200 g) are entered into a fluidized bed coating machine (Flow Coater Mini) and thereto is sprayed a coating liquid consisting of a mixture of Eudragit RS 30 D ® and Eudragit RL 30 D ® (95:5 by weight) (168 g), talc (25 g), acetyltributyl citrate (5 g) in water (234 g) with hot air-blowing of 60° C. Thereafter, the mixture is heat-treated at 60° C. to give controlled release granules (280 g) containing chlorpheniramine maleate.

Experiment (1) Preparation of pharmaceutical preparation:

Nonpareil 103 (particle size: 500-710 μm, 200 g) was entered and rolled in a centrifugal fluidized granulator (CF-360 EX), and thereto was gradually added a mixture of theophylline fine powder (120 g) and succinic acid (200 g) while spraying a 25% sucrose-containing water-ethanol (3:1), by which the nonpareil was surrounded with the powder coating to give theophylline-containing granules.

The theophylline granules thus prepared were entered into a fluidized bed coating machine (Flow Coater Mini) and thereto was sprayed an aqueous dispersion containing Eudragit RS ® (12 w/w %), talc (6 w/w %), triethyl citrate (1 w/w %) at 60° C. with controlling the spray amount so as to give various coating films having different coating amount. Thereafter, the mixture was heat-treated at 60° C. to give controlled release theophylline-containing granules having various amounts of coating film.

In the same manner as described above except that no organic acid was used, there were prepared theophylline-containing granules as a control.

(2) Comparison of the pattern of dissolution and release:

Each preparation obtained above was subjected to the test for dissolving and releasing by Paddle method (at 37° C., water, 100 rpm) as described in 11th Revised Japan Pharmacopeia.

(3) Results:

The results are shown in the accompanying FIG. 1. As is clear from the results, the preparation of this invention showed release of the pharmaceutically active substance with high release rate after the lag time even in the different coating amounts.

Effects of the Invention

The pharmaceutical preparation of this invention is coated with water-slightly permeable coating film, and hence, the pharmaceutically active substance is not dissolved and released until a fixed period of time elapses, but when the body fluid is gradually penerated into the preparation and thereby the organic acid is dissolved, the water-slightly permeable polymer is rapidly changed to water-permeable, which results in rapid dissolution and release of the pharmaceutically active substance.

The dissolution and release pattern of the pharmaceutically active substance owing to the change of the structure of the coating film is not observed in the preparation coated with a solution of the acrylic polymer in an organic solvent, but the specific dissolution and release phenomenon is characteristic in the preparation having the coating film formed with the aqueous dispersion as used in this invention.

The mechanism of such a unique dissolution and release pattern of the active substance in the pharmaceutical preparation of this invention is not clarified, but is assumed such that the dissolved organic acid reacts with the trimethylammonium-ethyl group contained in the coating film formed by the aqueous dispersion and thereby the waters-lightly permeable polymer is changed to a water-permeable polymer.

Besides, by varying the ratio of the coating film to the organic acid in the preparation of this invention, the degree of changing of from the water-slightly permeable polymer to the water-permeable polymer can be controlled, and thereby, the rate of dissolution and release of the pharmaceutically active substance can also be controlled. That is, by selecting appropriately the amount of the coating film and further the ratio of the coating film to the organic acid, the desired pattern of dissolution and release of the pharmaceutically active substance can be obtained.

The controlled release pharmaceutical preparation of this invention can be administered as it stands, but may be administered in the form of capsules filled with granules, fine granules or the like of the preparation.

Moreover, the pharmaceutical preparation of this invention can maintain the desired blood level of the pharmaceutically active substance for a long period of time after the initiation of the dissolution and release thereof, and hence, when it is used in combination with a conventional rapid-release preparation, it can maintain the desired blood level of the active substance for 24 hours even by one time administration.

What is claimed is:

1. A controlled release pharmaceutical preparation which comprises (a) a core containing an orally acceptable pharmaceutically active substance and succinic acid, and (b) a coating film formed on the surface of the core by coating with an aqueous dispersion of a water-insoluble and water-slightly permeable acrylic copolymer of ethyl acrylate, methyl methacrylate and trimethylammonium-ethyl methacrylate chloride.

2. The preparation according to claim 1, wherein the succinic acid and the copolymer composing the coating film are contained in the ratio of 1:0.3 to 1:10 by weight.

3. The preparation according to claim 2, wherein the ratio of the succinic acid and the copolymer is in the range of 1:0.4 to 1:5 by weight.

4. The preparation according to claim 1, wherein the core has an average particle size of about 300 μm to about 2,000 μm.

5. A method for producing a controlled release pharmaceutical preparation, which comprises coating a core containing an orally acceptable pharmaceutically active substance and succinic acid with an aqueous dispersion of a water-insoluble and water-slightly permeable acrylic copolymer of ethyl acrylate, methyl methacrylate and trimethylammonium-ethyl methacrylate chloride.

6. The method according to claim 5, wherein the succinic acid and the copolymer composing the coating film are contained in the ratio of 1:0.3 to 1:10 by weight.

7. The method according to claim 6, wherein the ratio of the succinic acid and the copolymer is in the ratio of 1:0.4 to 1:5 by weight.

8. The method according to claim 5, wherein the core has an average particle size of about 300 μm to about 2,000 μm.

9. A controlled release pharmaceutical preparation prepared by the process of claim 5.

10. The preparation according to claim 9, wherein the succinic acid and the copolymer composing the coating film are contained in the ratio of 1:0.3 to 1:10 by weight.

11. The preparation according to claim 10, wherein the ratio of the succinic acid and the copolymer is in the range of 1:0.4 to 1:5 by weight.

12. The preparation according to claim 9, wherein the core has an average particle size of about 300 μm to about 2,000 μm.

* * * * *